United States Patent [19]

Liu et al.

[11] Patent Number: 5,456,851
[45] Date of Patent: Oct. 10, 1995

[54] KETOCONAZOLE SHAMPOO CONTAINING BUTYLATED HYDROXYTOLUENE OR BUTYLATED HYDROXYANISOLE

[75] Inventors: Jue-Chen Liu, Neshanick; Jonas C. T. Wang, Robbinsville; Mohammed Yusuf, Edison, all of N.J.

[73] Assignee: Johnson & Johnson Consumer Products, Inc., Skillman, N.J.

[21] Appl. No.: 224,382

[22] Filed: Apr. 7, 1994

[51] Int. Cl.$^6$ .................................................. C11D 3/48
[52] U.S. Cl. .................. 252/106; 252/173; 252/174.11; 252/174.23; 252/544; 252/547; 252/551; 252/555; 252/399; 252/DIG. 13; 514/852; 514/881
[58] Field of Search ..................... 252/89.1, 106, 252/542, 544, 547, 550, 551, 555, DIG. 13, 174.11, 174.23, 399; 514/852, 881

[56] References Cited

U.S. PATENT DOCUMENTS

| | | | |
|---|---|---|---|
| 4,608,392 | 8/1986 | Jacquet et al. | 514/844 |
| 5,061,700 | 10/1991 | Dow et al. | 514/169 |
| 5,310,545 | 5/1994 | Eisen | 424/49 |

FOREIGN PATENT DOCUMENTS

WO92/00057  1/1992  WIPO.

OTHER PUBLICATIONS

Berger et al., "Double-Blind Placebo-Controlled Trial of Ketoconazole 2% Shampoo in the Treatment of Moderat to Severe Dandruff", Adv. Ther., 7(5), Sep./Oct. 1990, pp. 247–256.

Go et al., "A Double-Blind Trial of 1% Ketoconazole Shampoo Versus Placebo in the Treatment of Dandruff", Mycoses, 35(3–4), 1992, pp. 103–105.

Danby et al., "A Randomized Double-Blind, Placebo-Controlled Trial of Ketoconazole 2% Shampoo Versus Selenium Sulfide 2.5% Shampoo . . . ", Journal of the American Academy of Dermatology, 29(6), Dec. 1993, pp. 1008–1012.

Primary Examiner—Paul Lieberman
Assistant Examiner—Lorna M. Douyon
Attorney, Agent, or Firm—Charles J. Metz

[57] ABSTRACT

A shampoo that contains ketoconazole, a surfactant, a foaming agent, thickener sufficient to give the final formulation a viscosity in the range of about 4,000 to about 9,000 cps at room temperature (i.e., about 20°–25° C.), preservative, butylated hydroxytoluene or butylated hydroxyanisole in an amount sufficient to retard degradation of the ketoconazole, and acid, base or buffer sufficient to give the final composition a pH in the range of from about 4 to about 10.

14 Claims, No Drawings

KETOCONAZOLE SHAMPOO CONTAINING BUTYLATED HYDROXYTOLUENE OR BUTYLATED HYDROXYANISOLE

The invention relates to a ketoconazole-containing shampoo having improved stability.

BACKGROUND OF THE INVENTION

Ketoconazole is the generic name for the compound (±)-cis-1-acetyl-4-[4-[[2-(2,4-dichlorophenyl)-2-(1H-imidazol-1-ylmethyl)-1,3-dioxolan-4-yl]methoxy]phenyl]piperazine, having the formula:

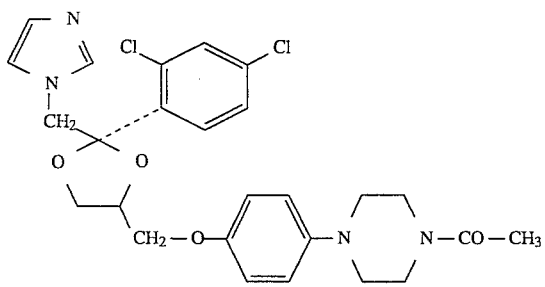

Ketoconazole was originally described by Heeres et al., for instance, in U.S. Pat. No. 4,335,125, in which its principal utility was as an antifungal compound. Ketoconazole was also disclosed by Rosenberg et al. in U.S. Pat. No. 4,569,935 to be useful in the topical treatment of psoriasis and seborrheic dermatitis. Pursuant to this utility, ketoconazole has been marketed in a 2% shampoo formulation (available in the United States by prescription only) for the treatment of scaling due to dandruff. The components of this shampoo include coconut fatty acid diethanolamide, disodium monolauryl ether sulphosuccinate, colorant such as F.D. & C. Red No. 40, hydrochloric acid and/or sodium hydroxide to control pH, imidurea, laurdimonium hydrolyzed animal collagen, macrogol 120 methyl glucose dioleate, perfume bouquet, purified water, sodium lauryl ether sulphate, and ketoconazole (2%).

Although the above-described shampoo is efficacious for dandruff treatment, it was desired to improve its cosmetic attributes such as lathering and conditioning, and to develop an efficacious formulation that, if desired, could contain less than 2% ketoconazole. However, since ketoconazole is subject to slow degradation by oxidation and hydrolysis, any formulation that contains significantly less than 2% ketoconazole must be effectively stabilized in order to have an acceptable shelf life. The present invention is based on the discovery of a formulation for a ketoconazole-containing shampoo that exhibits excellent cosmetic attributes such as lathering and conditioning, and is acceptably stable to degradation so that, if desired, the shampoo can be formulated to contain less than 2% ketoconazole.

BRIEF SUMMARY OF THE INVENTION

The present invention provides an aqueous shampoo that contains ketoconazole, a surfactant, a foaming agent, thickener sufficient to give the final formulation a viscosity in the range of about 4,000 to about 9,000 cps at room temperature (i.e., about 20°–25° C.), preservative, an antioxidant selected from the group consisting of butylated hydroxytoluene and butylated hydroxy anisole in an amount sufficient to retard degradation of the ketoconazole, and acid, base or buffer sufficient to give the final composition a pH in the range of from about 4 to about 10, preferably from about 6.5 to about 8, and more preferably from 6.9 to 7.4.

THE PRIOR ART

Butylated hydroxytoluene, whose proper chemical name is 2,6-bis (1,1-dimethylethyl)-4-methylphenol, also 2,6-di-tert-butyl-p-cresol or 2,6-di-tert-butyl-4-methylphenol, is marketed as an antioxidant for food, animal feed, petroleum products, synthetic rubbers, plastics, animal and vegetable oils, and soaps, and as an antiskinning agent in paints and inks. (Ref. - Page 238 of the Merck Index, Eleventh Edition.)

Butylated hydroxyanisole, whose proper chemical name is 2(3)-tert-butyl-4-methoxyphenol, is marketed as an antioxidant, especially for food. (Ref. - Page 1547 of the Merck Index, Eleventh Edition.)

DETAILED DESCRIPTION OF THE INVENTION

The shampoo of the invention contains ketoconazole, at least one surfactant, a foaming agent, thickeners sufficient to give the final formulation a viscosity in the range of about 4,000 to about 9,000 cps at room temperature, preservatives including butylated hydroxytoluene sufficient to prevent degradation of the final composition, and acid, base or buffer sufficient to give the final composition a pH in the range of from about 4 to about 10. Each class of ingredients will be discussed in turn.

Ketoconazole is employed in the shampoo in an amount effective to combat scaling due to dandruff. An effective amount will usually be found within the range of from about 0.3 weight percent up to about 3 weight percent, based on weight of the entire shampoo formulation. Preferred amounts are usually found within the range of from about 0.8 to 2 weight percent, and more preferably from about 0.9 to about 1.1 weight percent. At concentrations below the indicated range, the effectiveness begins to diminish to unacceptable levels, and at concentrations higher than about 3 weight percent, the limited solubility of ketoconazole in aqueous media, even with surfactants present, becomes a significant factor.

The shampoo of the invention contains one or more surfactants, which are employed principally as cleansing agents. Specific illustrations of surfactants that have been found to be useful include the following compositions:

Sodium laureth sulfate, a composition having the formula $CH_3(CH_2)_{10}CH_2(OCH_2CH_2)_nOSO_3Na$, wherein n represents a number having an average value of from 1 to 4; and Sodium cocoyl sarcosinate, which is the sodium salt of cocoyl sarcosine. Cocoyl sarcosine is the coconut oil fatty acid amide of sarcosine (N-methylglycine or methylaminoethanoic acid). Coconut fatty acid is a mixture of myristic acid, lauric acid, palmitic acid and stearic acid.

Other surfactants that can be employed in the shampoo of the invention include sodium $C_{14-16}$ olefin sulfonates, sodium lauryl sulfate, cocamidopropylamine oxide, lauramido DEA (lauramido diethanolamine), cocamidopropyl betaine, disodium oleamido MIPA sulfosuccinate, disodium cocamido MIPA sulfosuccinate, disodium laureth sulfosuccinate, cocoamphocarboxy-glycinate, and disodium oleamido MEA sulfosuccinate. These surfactants are all known in the shampoo and cosmetic arts.

The shampoo of the invention also contains foaming agents such as fatty acid mono- and di-alkanolamides, for instance, cocamide MEA (a mixture of coconut acid monoethanolamides of the formula $R\text{-}CO\text{-}NHCH_2CH_2OH$ wherein R represents the residue after removal of the carboxyl group of coconut fatty acid), cocamide DEA [a mixture of diethanolamides of the formula $R\text{-}CO\text{-}N(CH_2CH_2OH)_2$ wherein R is as defined above], oleamide MEA and oleamide DEA.

The shampoo of the invention contains a thickener to impart a viscosity to the formulation in the range of from about 4,000 to about 9,000 cps at room temperature. Such thickeners include Carbopol 1342, which is a copolymer of $C_{10-30}$alkyl acrylates, acrylic acid and/or methacrylic acid, cross-linked with an allyl ether of sucrose. Other thickeners that can be used include cellulose derivatives such as hydroxypropyl methylcellulose, hydroxyethyl cellulose, carboxymethyl cellulose, and the like. The addition of a small amount of salt (NaCl) also serves to control the viscosity of the final formulation. Usually, the amount of salt added will be within the range of from about 0.25 to 0.6 weight percent.

The preservatives that can be used in the shampoo of the invention include tetrasodium EDTA (the tetrasodium salt of ethylenediamine tetraacetic acid-used as a chelating agent to protect against degradation caused by metal ions and also to enhance anti-bacterial activity) and quaternium-15 [1-(3-chloroallyl)-3,5,7-triaza-1-aziona-adamantane chloride - used as an antimicrobial agent]. Other preservatives that can be used include paraben, Kathon CG biocide (a mixture of 5-chloro-2-methyl-4-isothiazolin-3-one and 2-methyl-4-isothiazolin-3-one), phenoxyethanol, benzyl alcohol, and the like.

An important feature of the present invention is the discovery that a carefully controlled amount of an antioxidant selected from the group consisting of butylated hydroxytoluene ("BHT") and butylated hydroxyanisole ("BHA") is effective to stabilize the ketoconazole present in the shampoo against degradation during accelerated aging for 13 weeks at 50° C., which is considered to be predictive of performance during storage at ambient temperatures for two years. Effective stability is considered to be a loss of active ingredient (in this case, ketoconazole) during storage of not more than about 10 percent. The proportion of BHT or BHA that has been found to be most effective is within the range of from about 0.01 to about 1, and preferably 0.1±0.025, weight percent, based on weight of the entire shampoo formulation (See Table 1, below). Surprisingly, proportions greater than this amount do not stabilize as effectively for the 13-week accelerated aging period, although if one extends the accelerated aging period longer than 13 weeks, greater proportions of BHT or BHA tend to be more effective, since the BHT or BHA itself is also subject to degradation (see Table 2, below). However, it is well recognized by government regulatory agencies and in the pharmaceutical and cosmetic industries that stability testing for 13 weeks at 50° C. is quite sufficient to predict product stability during normal shelf life storage for two (2) years at room temperature. It is also equally important that, for safety reasons (that is, to minimize the potential for skin sensitization), it is desired to use as small an amount as possible of BHT or BHA.

The shampoo of the invention can contain other materials such as fragrances, colorants, opacifiers, conditioners such as polyquaternium-7 [the polymeric quaternary ammonium salt of acrylamide and dimethyl diallyl ammonium chloride], pearlizing agents such as ethylene glycol distearate and ethylene glycol monostearate, etc., that are standard in shampoo formulations.

The shampoo contains acids, bases, and buffers, as needed to maintain a pH of from 4 to 10, and preferably from about 6.5 to 8, and more preferably from 6.9 to 7.4. (A neutral pH is desired in order to minimize the potential for skin sensitization.) The nature and mode of use of such materials are known in the art.

The components of the shampoo are employed in conventional amounts, for example:

(a) 36% to 45% surfactants, (b) 2% to 6% foaming agent, (c) 0.3% to 3% ketoconazole, (d) 0.2% to 1.3% thickener, (e) 0.01% to 1% BHT or BHA;

(f) preservatives sufficient to retard degradation of the final composition in order to give adequate shelf life, (g) acid, base or buffer to yield a pH in the desired range, and (h) water QS ad 100% (that is, sufficient water to make 100%).

Standard Preparation of Shampoo

A vessel was charged with a 1.64% stock solution of Carbopol 1342 (prepared using a Quadro disperser which functions by keeping the powdered polymer evenly divided and pulling the powder by a vacuum into a stream of water) and deionized water, and heated to about 70° C. Both surfactants, i.e. sodium laureth sulfate and sodium cocoyl sarcosinate, were added, followed by the foaming agent, cocamide MEA, and a pearlizing agent (ethylene glycol distearate) and mixed until complete dissolution. Then the BHT was added and the mixture was stirred until complete dissolution thereof. The solution was allowed to cool slightly, whereupon the antifungal ingredient ketoconazole was added while stirring well. (The ketoconazole is added while the pH is slightly acidic, to facilitate dissolution.) The mixture was allowed to cool to about 40° C., at which temperature there were added the conditioner (polyquaternium-7), the preservatives quaternium-15 and tetrasodium EDTA, the colorants and fragrances, and the NaCl for thickening the solution. The pH of the solution was adjusted to 6.9–7.4 with a 25% aq. solution of NaOH and deionized water was added to the final volume.

Using the general procedure described above, the following shampoo formulations were made:

EXAMPLE 1:

Shampoo Formulations for Normal Hair

| Ingredients | (a) | (b) |
|---|---|---|
| sodium laureth sulfate | 30 | 30 |
| sodium cocoyl sarcosinate | 10 | 10 |
| cocamide MEA | 4 | 4 |
| ketoconazole USP | 1 | 2 |
| glycol distearate | 1.25 | 1.25 |
| polyquaternium-7 | 1 | 1 |
| Carbopol 1342 | 0.6 | 0.6 |
| tetrasodium EDTA | 0.5 | 0.5 |
| perfume oil | 0.5 | 0.5 |
| sodium chloride | 0.3 | 0.3 |
| sodium hydroxide 25% | 0.92 | 0.9 |
| butylated hydroxytoluene | 0.1 | 0.1 |
| quaternium-15 | 0.05 | 0.05 |
| colorants | 0.001 | 0.001 |

-continued

| Ingredients | (a) | (b) |
|---|---|---|
| deionized water QS ad | 100 | 100 |

EXAMPLE 2:

Shampoo Formulations for Oily Hair

| Ingredients | (a) | (b) | (c) |
|---|---|---|---|
| sodium laureth sulfate | 33.33 | 33.33 | 33.33 |
| sodium cocoyl sarcosinate | 11 | 11 | 11 |
| cocamide MEA | 4 | 4 | 4 |
| ketoconazole USP | 1 | 1 | 2 |
| glycol distearate | 1.25 | 1.25 | 1.25 |
| polyquaternium-7 | 0.6 | 0.6 | 0.6 |
| Carbopol 1342 | 0.75 | 0.75 | 0.75 |
| tetrasodium EDTA | 0.5 | 0.5 | 0.5 |
| perfume oil | 0.5 | 0.5 | 0.5 |
| sodium chloride | 0.3 | 0.3 | 0.3 |
| sodium hydroxide 25% | 1.18 | 1.243 | 1.18 |
| butylated hydroxytoluene | 0.1 | 0.1 | 0.1 |
| quaternium-15 | 0.05 | 0.05 | 0.05 |
| colorants | 0.0053 | 0.0053 | 0.0053 |
| deionized water QS ad | 100 | 100 | 100 |

EXAMPLE 3:

Shampoo Formulations for Dry or Damaged Hair

| Ingredients | (a) | (b) | (c) |
|---|---|---|---|
| sodium laureth sulfate | 30 | 30 | 30 |
| sodium cocoyl sarcosinate | 10 | 10 | 10 |
| cocamide MEA | 4 | 4 | 4 |
| ketoconazole USP | 1 | 1 | 2 |
| glycol distearate | 1.25 | 1.25 | 1.25 |
| polyquaternium-7 | 5 | 5 | 5 |
| Carbopol 1342 | 0.5 | 0.5 | 0.5 |
| tetrasodium EDTA | 0.5 | 0.5 | 0.5 |
| perfume oil | 0.5 | 0.5 | 0.5 |
| sodium chloride | 0.4 | 0.4 | 0.3 |
| sodium hydroxide 25% | 0.7333 | 0.733 | 1.19 |
| butylated hydroxytoluene | 0.1 | 0.1 | 0.1 |
| quaternium-15 | 0.05 | 0.05 | 0.05 |
| colorants | 0.0018 | 0.0018 | 0.0018 |
| deionized water QS ad | 100 | 100 | 100 |

In all the formulations given above in Examples 1–3, the proportion of sodium hydroxide may vary slightly, to arrive at the more preferred pH level of 6.9 to 7.4, and the proportion of salt (NaCl) may vary, to arrive at the desired viscosity.

EXAMPLE 4:

Stability Studies

The formulation described above as Example 1 (a) [Shampoo formulation for normal hair containing 1% ketoconazole] was subjected to stability studies, as follows:

Shampoo formulations containing 0, 0.01, 0.1, 0.4, 0.7 and 1.0 weight % BHT were stored at 50° C. for 24 weeks. At 0, 4, 8, 12, 16, 20 and 24 weeks, samples were taken from each formulation and analyzed for ketoconazole content. The table below reports the percentage of ketoconazole remaining for each sample after the indicated number of weeks:

TABLE 1

Percent of original proportion of ketoconazole remaining Stability analyses at 50° C. for the 24 weeks is indicated as follows

| Week | 0.0%[1] | 0.01% | 0.1% | 0.4% | 0.7% | 1.0% |
|---|---|---|---|---|---|---|
| 0 | 100 | 100 | 100 | 100 | 100 | 100 |
| 4 | 97.98 | 99.01 | 101.12 | 102.00 | 101.23 | 101.89 |
| 8 | 97.18 | 97.75 | 98.84 | 101.07 | 100.78 | 102.77 |
| 12 | 85.61 | 92.30 | 99.48 | 96.35 | 94.49 | 95.91 |
| 16 | 88.49 | 88.80 | 95.93 | 93.01 | 93.24 | 93.27 |
| 20 | 82.22 | 84.75 | 87.17 | 90.29 | 89.91 | 93.27 |
| 24 | 82.12 | 84.13 | 86.44 | 89.46 | 92.82 | 90.68 |

[1]Percent BHT in original sample.
Note - the relative standard deviation for all but two samples was less than 2%.

The samples were also analyzed for BHT content after storage for 24 weeks at 4° C. and at 50° C. The results are displayed in the following table:

TABLE 2

| | BHT analysis | |
|---|---|---|
| FORMULATED % BHT | 4° C. 24 wks. % BHT | 50° C. 24 wks. % BHT |
| 1.0% | 0.940% | 0.277% |
| 0.7% | 0.583% | 0.218% |
| 0.4% | 0.352% | 0.107% |
| 0.1% | 0.084% | 0.023% |
| 0.01% | 0.009% | 0.005 |
| 0.0% | 0 | 0 |
| PLACEBO[2] | 0.0968% | 0.0631% |

[2]Contained 0.1% BHT and no ketoconozole.

What is claimed is:

1. An aqueous shampoo that contains ketoconazole in an amount within the range of from about 0.3 weight percent to about 3 weight percent, based on weight of the shampoo, to combat scaling due to dandruff, a surfactant, a foaming agent, thickener sufficient to give the final formulation a viscosity in the range of about 4,000 to about 9,000 cps at room temperature, an antioxidant in an amount from 0.01 to 1 weight percent selected from the group consisting of butylated hydroxytoluene and butylated hydroxyanisole to retard degradation of the ketoconazole, acid, base or buffer sufficient to give the shampoo a pH in the range of from about 4 to about 10 and preservative sufficient to retard degradation of the final composition.

2. The shampoo of claim 1 wherein the pH is in the range of from about 6.5 to about 8.

3. The shampoo of claim 2 wherein the pH is in the range of from about 6.9 to 7.4.

4. The shampoo of claim 1, 2 or 3 wherein the antioxidant is butylated hydroxytoluene employed in an amount of 0.1±0.025 weight percent, based on weight of the shampoo.

5. The shampoo of claim 1 wherein the ketoconazole is employed in an amount within the range of from about 0.8 weight percent to about 2.0 weight percent, based on weight of the shampoo.

6. The shampoo of claim 5 wherein the ketoconazole is employed in an amount within the range of from about 0.9 weight percent to about 1.1 weight percent, based on weight of the shampoo.

7. A shampoo according to claim 1 comprising one or more surfactants selected from the group consisting of sodium $C_{14-16}$ olefin sulfonates, sodium lauryl sulfate, sodium laureth sulfate, cocamidopropylamine oxide, lauramido diethanolamine, cocamidopropyl betaine, sodium cocoyl sarcosinate, disodium oleamido monoisopropanolamine sulfosuccinate, disodium cocamido monoisopropanolamine sulfosuccinate, disodium laureth sulfosuccinate, cocoamphocarboxy-glycinate, disodium oleamido monoethanolamine sulfosuccinate.

8. A shampoo according to claim 1 wherein the foaming agent is selected from the group of fatty acid mono- and di-alkanolamides consisting of cocamide monoethanolamine, cocamide diethanolamine, oleamide monoethanolamine and oleamide diethanolamine.

9. A shampoo according to claim 1 that additionally contains polyquaternium-7 as a conditioner.

10. A shampoo according to claim 1 further comprising one or more pearlizing agents selected from the group consisting of ethylene glycol distearate and ethylene glycol monostearate.

11. A shampoo according to claim 1 further comprising one or more fragrances and one or more colorants.

12. A shampoo according to claim 1 comprising by weight based on the total weight of the formulation approximately:
  (a) 36% to 45% surfactants,
  (b) 2% to 6% foaming agent,
  (c) 0.3% to 3% ketoconazole,
  (d) 0.2% to 1.3% thickener,
  (e) 0.1% to 1% butylated hydroxytoluene antioxidant;
  (f) preservatives sufficient to retard degradation of the final composition,
  (g) acid, base or buffer to yield a pH in the range of from 6.9 to 7.4, and
  (h) water QS ad 100%.

13. A shampoo according to claim 12 comprising by weight based on the total weight of the formulation approximately:
  (a) 36% to 45% surfactants,
  (b) 2% to 6% foaming agent,
  (c) 0.3% to 3% ketoconazole,
  (d) 0.4% to 8% conditioner,
  (e) 0.2% to 1.3% thickener,
  (f) 1% to 1.5% pearlizing agent,
  (g) 0.5% to 1% preservative(s),
  (h) 0.1±0.025% butylated hydroxtoluene antioxidant,
  (i) acid, base or buffer to yield a pH in the range of 6.9 to 7.4,
  (j) fragrance(s) and colorant(s), and
  (k) water QS ad 100%.

14. A process of preparing a shampoo formulation that contains ketocanazole in an amount within the range of from about 0.3 weight percent to about 3 weight percent, based on weight of the shampoo to combat scaling due to dandruff, a surfactant, a foaming agent, thickener sufficient to give the final formulation a viscosity in the range of about 4,000 to about 9,000 cps at room temperature, an antioxidant in an amount from 0.01 to 1 weight percent selected from the group consisting of butylated hydroxytoluene and butylated hydroxyanisole to retard degradation of the detoconazole, acid, base or buffer sufficient to give the shampoo a pH in the range of from about 4 to about 10, and preservative sufficient to retard degradation of the final composition, said process comprising the steps of:
  (a) heating a solution of thickener and deionized water,
  (b) mixing the surfactants, the foaming agent and optionally the pearlizing agent with the solution of (a),
  (c) mixing the butylated hydroxytoluene or butylated hydroxyanisole with the solution of (b),
  (d) mixing the antifungal ketoconazole with the solution of (c),
  (e) allowing the solution of (d) to cool somewhat and mixing therewith the preservative(s) and the sodium chloride for thickening, and optionally the conditioner, the fragrance(s) and colorant(s),
  (f) adding acid, base or buffer to the solution of (e) to yield a pH in the range of 4 to 10, and
  (g) adding deionized water to the solution of (f) to 100%.

* * * * *